United States Patent
Fleming et al.

(10) Patent No.: US 6,596,284 B1
(45) Date of Patent: Jul. 22, 2003

(54) TREATING ECZEMA WITH A COMBINATION OF ISOTONIC SALINE OCEAN® AND NASAL MAST CELL STABILIZERS

(76) Inventors: Thomas E. Fleming, 24 Bopp Ln, St. Louis, MO (US) 63131; Theodore H. Feller, 11834 Conway Rd., St. Louis, MO (US) 63131

( * ) Notice: Subject to any disclaimer, the term of this patent is extended or adjusted under 35 U.S.C. 154(b) by 0 days.

(21) Appl. No.: 10/063,493

(22) Filed: Apr. 30, 2002

(51) Int. Cl.$^7$ .................................................. A61K 9/00
(52) U.S. Cl. ........................................ 424/400; 514/861
(58) Field of Search ........................... 424/400; 514/861

(56) References Cited

U.S. PATENT DOCUMENTS

| | | |
|---|---|---|
| 1,144,906 A | 6/1915 | Fitzmaurice et al. |
| 3,419,578 A | 12/1968 | Klatt et al. ............... 260/345.2 |
| 3,962,308 A | 6/1976 | Sinkula .................. 260/465 D |
| 3,993,679 A | 11/1976 | Hall et al. ............... 260/465 D |
| 4,145,438 A | 3/1979 | Kingsley et al. ............ 424/283 |
| 4,269,835 A | 5/1981 | Whittle ........................ 424/247 |
| 4,271,182 A | 6/1981 | Sullivan ...................... 424/283 |
| 4,409,237 A | 10/1983 | Cairns et al. ............... 424/283 |
| 4,526,899 A | 7/1985 | Stevenson .................... 514/456 |
| 5,475,023 A | 12/1995 | Baskeyfield et al. ........ 514/456 |

FOREIGN PATENT DOCUMENTS

| | | |
|---|---|---|
| EP | 0413583 A2 | 8/1990 |
| GB | 1399334 | 7/1975 |
| WO | WO 90/13284 | 11/1990 |

OTHER PUBLICATIONS

Horan RF, Schneider LC, Sheffer AL, JAMA 268:2858 (1992).

Karmali, RA, Safai B. Prostaglandins Leukotrienes & Medicine 15:277–286 (1984).

Bos JD, Wierenga EA, Smitt JHS et al. Arch Dermatol 128:1509 (1992).

Susan Budavari, et al., "An Encyclopedia of Chemicals, Drugs, and Biologicals", 11 th Edition (1989).

*Primary Examiner*—Michael G. Hartley
*Assistant Examiner*—Konata M. George
(74) *Attorney, Agent, or Firm*—Rashida A. Karmali

(57) ABSTRACT

The present invention relates to the prevention and treatment of atopic dermatitis and treatment of atopic dermatitis and other eczematous disorders by application of topical mast cell stabilizers including cromolyn sodium, nedocromil or lodoxamide, in a vehicle of a buffered isotonic saline solution (OCEAN®).

4 Claims, No Drawings

TREATING ECZEMA WITH A COMBINATION OF ISOTONIC SALINE OCEAN® AND NASAL MAST CELL STABILIZERS

BACKGROUND OF INVENTION

The present invention relates to prevention and treatment of eczema and atopic dermatitis. More particularly, the present invention relates to the prevention and treatment of atopic dermatitis and other eczematous disorders by the application of a combination of topical isotonic saline OCEAN® and topical nasal mast cell stabilizers.

Atopic dermatitis is a chronic inflammatory skin disorder, also known by terms used to describe the disorder as neurodermatitis, disseminated lichen simplex chronicus, or atopic eczema. The prevalence of atopic dermatitis among persons one year to seventy four years of age ranges from seven to twenty four cases per one thousand. Atopic dermatitis is most prevalent in infancy and childhood, less prevalent in puberty, and often persists into adulthood. Horan R F, Schneider L C, Sheffer A L, JAMA 268:2858 (1992).

Atopic dermatitis is not a primary allergic disorder per se but appears to be inherited in association with certain allergic disorders. Environmental stimuli can trigger the disease in genetically predisposed individuals. The increased prevalence of atopic dermatitis since the 1990s has been attributed to environmental irritants, infections, previous exposure to allergic foods, and airborne allergens such as dust, mites, animal dander and pollens.

Atopy is characterized by physiologic, immuno pathologic, and pharmacological abnormalities that involve the skin. These abnormalities include: 1) a lowered threshold to itch stimuli, 2) a hypersensitivity to alpha-adrenergic agonists and to cholinergic agents, 3) a very dry hyperkeratotic skin which has decreased water-holding capacity, 4) a marked tendency to produce lichenification in response to friction and scratching, and 5) a tendency for the skin to be colonized with bacteria. Immunopathologic abnormalities involve interaction of many cells (mast cells, basophils, eosinophils, keratinocytes, Langerhans cells, and helper T cells) and cell products (histamine, leukotrienes, prostaglandins and cytokines) that participate in the inflammatory cascade. Karmali R A, Safai B. Prostaglandins Leukotrienes & Medicine 15: 277–286 (1984). Enhanced production of serum IgE in conjunction with the binding of IgE to epidermal Langerhans cells may induce an eczematous reaction in the skin via allergen-specific T cell responses. Dysregulation of IgE synthesis in the pathogenesis of atopic dermatitis points to abnormalities of cell-mediated as well as of humoral immunity. Bos J D, Wierenga E A, Smitt J H S, et al. Arch Dermatol 128: 1509 (1992).

Mast cells are also implicated in the pathogenesis of IgE-mediated food hypersensitivity. Histamine activation of Hl receptors increases vascular permeability, which results in passage of serum factors and leukocytes into the skin, where mediators of inflammation are released. It is likely that the release of mast cell mediators, including histamine, is responsible for the pruritus and subsequent eczematous skin findings in patients with atopic dermatitis.

CLINICAL FEATURES

Itching is the primary symptom of atopic dermatitis. The pruritus may be generalized or localized, seasonal and often worse in winter, and has a diurnal rhythm in which itching is minimal at midday and maximal in the evening. Emotional stress can also provoke and aggravate itching and scratching.

Excoriations, papules, eczema, and lichenification are the lesions of atopic dermatitis.

CLINICAL COURSE

The clinical course of atopic dermatitis is divided into three stages: the infantile stage, the childhood stage and the adolescent/adult stage. The diagnosis of atopic dermatitis is usually clinically evident. Secondary skin infections may result due to localized immunosuppression in the skin. For example, in atopic dermatitis, there is increased susceptibility to herpes simplex, herpes zoster, staphylococcal impetiginization, and infection with human papillomavirus.

A severe complication of atopic dermatitis, Kaposi's varicelliform eruption is characterized by hemorrhagic vesicles, high fever, and severe prostration. The etiologic agents are herpes simplex virus (eczema herpeticum), vaccinia virus (eczema vaccinatum) and coxsackievirus A16.

Lesions of atopic dermatitis occasionally progress to generalized erythroderma, usually seen in adults, and accounts for 4.5 percent of exfoliative dermatitis cases.

A much less common but serious complication is the development of cataracts in patients with long-standing atopic dermatitis. The long-term application of topical corticosteroids to the eyelids and periorbital skin can also increase the risk of ocular cataract. Regular eye examinations are recommended in children with atopic dermatitis.

Currently, mast cell stabilizers are employed to treat allergic rhinitis and asthma. In response to a challenge by an allergen, mast cells release mediators which include, histamine, leukotrienes, prostaglandins, serotonin, proteases and others, which induce vasodilatation, smooth muscle contraction, glandular secretion of stimulation of irritant nerve receptors among other symptoms. These mediators are also implicated as mediators for symptoms of atopic dermatitis and/or infections of wounds or skin lesions. Since mast cell stabilizers inhibit the release of the mediators from the mast cells, the present invention proposes a new use for the mast cell stabilizers in the treatment of atopic eczema and/or some infections of wounds or skin lesions. Suitable mast cells used include cromolyn sodium, nedocrormil and lodoxamide. Each of these mast cell stabilizers may be combined with a physiological solution, preferably an isotonic saline OCEAN® , alone and/or as mixtures in various combinations, and may be topically applied.

SUMMARY OF INVENTION

There is provided by the present invention a topical spray or topical drops for the treatment of atopic dermatitis, said topical preparations comprising an effective amount of a topical mast cell stabilizer to inhibit release of mast cell mediators, wherein the topical mast cell stabilizer is selected from the group consisting of cromolyn sodium, nedocromil and lodoxamide, and topical preparation includes sterile isotonic saline OCEAN®.

There is also provided by the present invention a topical spray for the treatment of other eczematous disorders, herpes simplex, herpes zoster, vaccinia virus or coxsackievirus, said topical spray comprising an effective amount of a mast cell stabilizer selected from the group consisting of cromolyn sodium, nedocromil and lodoxamide, and OCEAN®.

There is also provided by the present invention a topical spray to prevent wound formation and promote wound healing involving the repair or replacement of damaged tissues including, but not limited to, skin, vascular tissue or soft tissues.

DETAILED DESCRIPTION

Reduction of various factors that may incite or exacerbate an episode of atopic dermatitis and associated disorders, is of utmost importance. Some of these triggers are physical or chemical irritants, psychological stress, infections, overheating and allergens.

The prime objectives of treatment are to reduce inflammation and to prevent and relieve itching. Itching leads to scratching and to trauma of the skin, resulting in infection, lichenification, and eczematization. Three different therapeutic approaches are used systemic, phototherapy and topical therapy. For example, systemic therapy may include use of papaverine hydrochloride, antihistamines (hydroxyzine or diphenydramine), antibiotics, glucocorticoids, interferon gamma, or cyclosporine. Phototherapy usually involves use of UVB or UVA. Topical therapy includes corticosteroids, antihistamines, or emollients The present invention provides a topical preparation comprising an effective amount of a mast cell stabilizer, selected from a group consisting of cromolyn sodium, nedocromil and lodoxamide. This preparation may be used alone or optionally, in combination with any one or more conventional therapeutic approaches which use systemic, phototherapy and other topical therapies.

The topical mast cell stabilizers used herein, function by preventing or inhibiting the release of mediators by mast cells in response to various factors that trigger the mast cells. These factors when present, bind to the immunoglobulin on the surface of mast cells and trigger the release of the mediators. One skilled in the art will employ a sufficient amount of mast cell stabilizer effective to inhibit mast cell mediator release and no more. This amount varies depending on whether cromolyn sodium, nedocromil or lodoxamide is employed.

In the case of cromolyn sodium, the effect of topical cromolyn (disodium cromoglycate) ointment on atopic dermatitis is a subject of controversy. Topical cromolyn ointment was found to have no beneficial effect. However, cromolyn nebulizer solution with systemic anti-allergic medication was effective in treating severe facial atopic dermatitis in adults. The differences in response to topical cromolyn may be due to the differences in the ages of the subjects studied. Or, as shown in the present invention, the effect of topical sodium cromolyn is treatment of moderate to severe atopic dermatitis, is a function of the concentration and stability of the sodium cromolyn formulation made for topical application.

In the case of cromolyn sodium, 0.5% to about 5.0%, and preferably 0.7% to about 1.4% is administered in combination with OCEAN®, every 4 to 12 hours.

OCEAN® is a 0.65% sodium chloride solution containing phenylcarbinol and benzalkonium chloride (Fleming & Co., Fenton, Mo. 63026). It is a buffered and isotonic solution. Cromolyn sodium is also known as disodium cromoglycate or simply "cromolyn". Cromolyn is the disodium salt of 1,3-bis-(2-carboxy-chromone-5"yloxy)2-hydroxy propane. The term cromolyn as used herein includes all structural analogs and functional derivatives of cromolyn as disclosed in the U.S. Pat. No. 3,419,578 which is hereby incorporated be reference. Functional derivatives of cromolyn include its salts, esters and amides, in particular the disodium salt of cromolyn e.g., disodium cromoglycate or cromolyn sodium.

The chemical names for cromolyn include: 5,5"-[(2-Hydroxy-1,3-propanediyl)bis(oxy)]bis[4-oxo-4H-1-benzopyran-2-carboxylic acid]; 5,5"-[(2-hydroxytrimethylene) dioxy]bis(4-oxo-4H-1-benzopyran-2-carboxylic acid);5,5"-(2-hydroxytrimethylenedioxy)bis(4-oxochromene-2-carboxylic acid);1,3-bis(2-carboxychromon-5-yloxy)-2-hydroxypropane; 1,3-di(2-carboxy-oxochromen-5-yloxy)propan-2-ol; and cromoglycic acid.

Its method of preparation is described in U.S. Pat. No. 3,419,578. and in U.S. Pat. No. 1,144,906.

Cromolyn is known to be useful for the treatment of allergic conditions for example, asthma, hay fever and conjunctivitis of allergic origin. It is believed to interface with the mechanism leading to a transiently elevated $Ca^{2+}$ upon antigenic stimulation of the cell. Hence, it prevents histamine release.

Nedocromil is given at a concentration of about 0.1% to about 8.0%. Nedocromil as used herein includes nedocromil and its pharmaceutically acceptable salts. The preferred salts are the sodium and calcium salts. Nedocromil, 9-ethyl-6,9-dihydro-4,6-dioxo-10-propyl-4H-pyrano [3,2-g] guinoline-2,8-dicarboxylic acid, inhibits the release and/or action of pharmacological mediators which result from the in vivo combination of certain types of antibodies and specific antigens, e.g., the combination of antibody with specific antigen. The preparation of nedocromil is described in U.S. Pat. No. 4,474,787 and by Cairns et al., J.Med.Chem.28:1832(1985) (incorporated by reference herein).

Lodoxamide is administered at a concentration of from about 0.1% to about 10% and preferably from about 5 to about 60 mg/ml. Lodoxamide as used herein includes lodoxamide and its pharmaceutically acceptable salts and esters. The preferred salt of lodoxamide is its di-tris (hydroxymethyl)methyl ammonium(or bisTHAM) salt and the preferred ester is the ethyl ester. Lodoxamide is known to inhibit the release of mast cell mediators of inflammation. The manufacture of lodoxamide, N,N"(2-chloro-5-cyano-m-phenylene) dioxamic acid, is taught in U.S. Pat. No. 3,962, 308 and U.S. Pat. No. 3,993,679 (incorporated by reference, herein).

In general, additives will be added as needed, for example, antimicrobial agent, antioxidant, isotonic agent, solubilizing agent, viscocity builder or surface active agent. The Ph range is maintained around 6.5. Aerosol formulations and topical drops are prepared as per known techniques. The OCEAN employed is of an appropiate pharmaceutical grade. These formulations may be administered by drop or spray every 4 to 6 hours to obtain the desired relief.

EXAMPLE

Wound healing is a complex process including an initial proliferative phase during which there is rapid cell metabolism and proliferation, disposal of debris, moblization of fibroblasts and restoration of circulation. It is during this degranulation period that the wound is most susceptible to infection. The subsequent phase of wound healing involves development of collagen and tensile strength. Hence, there must be a balance between promotion of the proliferative phase and the onset of the tensile phase during the wound healing in different conditions, including, but not limited to, infections after surgery, skin grafting, surgery wound breakdown, ulcers, pressure sores, decubitis, compromised amputation or surgical sites, after shave, dental work, diabetic ulcers, sunburns, diabetic skin sores, or distinction of tissue by radiation.

The present invention provides suitable preparations of sodium cromolyn, nedocromil, lodoxamide, and other mast cell stabilizers, to promote the degranulation phase of wound healing and therefore, enhance the wound healing process.

In the diabetics, the breakdown of the foot is common due to a combination of neuropathy, infection and vascular impairment.

In the elderly patients, pressure ulcers continue to be a major healthcare problem especially in patients with limited mobility. The risk of death increases when a pressure ulcer develops. Burns are common and may be of different wound severities. Skin grafting is usually an option for burn patients. The compositions of the present invention are suitable for accelerating wound healing in ulcers associated with diabetics, in pressure ulcers and or in burn patients.

The following examples are given for purposes of illustration only and not by way of limitation on the scope of the invention.

A group of twenty adult subjects suffering from atopic eczema were asked to apply cromolyn sodium (at a concentration of 300 mg/45 ml OCEAN® giving a concentration of 0.67%) every 4 to 6 hours at the affected site, and instructed to rub the solution gently into the lesion. After two weeks, 19 of the 20 subjects experienced relief from the symptoms.

One adult patient having a history of stress-induced eczema was ready to try anything after experiencing a worsening of symptoms with a number of steroid creams. This subject experienced relief from rubbing cromolyn in OCEAN every 6 hours, and especially during the evening hours. After 7 days, the eczematous site was healed and new and softer skin emerged. However, when the topical application was stopped, the itching started again. Therefore, the topical treatment must be continued as long as needed.

The present invention is not to be limited in scope by the specific embodiments described which are intended as single illustrations of individual aspects of the invention, and functionally equivalent methods and components are within the scope of the invention, in addition to those shown and described herein will become apparent to those skilled in the art from the foregoing description. Such modifications are intended to fall within the scope of the appended claims.

What is claimed is:

1. A topical preparation suitable for application as spray or drops, said preparation comprising an effective amount of a topical mast cell stabilizer to inhibit release of mast cell mediators, and said topical mast cell stabilizer selected from the group consisting of cromolyn sodium, nedocromil and lodoxamide, and an isotonic solution containing 0.65% sodium chloride in water with phenylcarbinol and benzalkonium chloride.

2. The preparation of claim 1, wherein the effective amount of cromolyn sodium in the range of a concentration of 0.5% to 5.0%.

3. The preparation of claim 1, wherein the effective amount of nedocromil is in the range of a concentration of 0.1% to 8.0%.

4. The preparation of claim 1, wherein the effective amount of lodoxamide is in the range of a concentration of 0.1% to 10%.

* * * * *